(12) United States Patent
Chapman et al.

(10) Patent No.: US 8,277,618 B2
(45) Date of Patent: Oct. 2, 2012

(54) ELECTROCHEMICAL CELL

(75) Inventors: Conrad S. Chapman, Liverpool (GB);
Constant M. G. Van Den Berg,
Liverpool (GB)

(73) Assignee: The University of Liverpool, Liverpool (GB)

( * ) Notice: Subject to any disclaimer, the term of this patent is extended or adjusted under 35 U.S.C. 154(b) by 666 days.

(21) Appl. No.: 12/227,262

(22) PCT Filed: May 9, 2007

(86) PCT No.: PCT/GB2007/001704
§ 371 (c)(1),
(2), (4) Date: Sep. 18, 2009

(87) PCT Pub. No.: WO2007/135363
PCT Pub. Date: Nov. 29, 2007

(65) Prior Publication Data
US 2010/0224489 A1    Sep. 9, 2010

(30) Foreign Application Priority Data

May 19, 2006  (GB) .................................. 0609926.1

(51) Int. Cl.
*C25D 17/00*    (2006.01)

(52) U.S. Cl. .................. 204/222; 204/196.38; 204/400; 204/286.1; 204/412

(58) Field of Classification Search .................. 204/222, 204/412, 435, 286
See application file for complete search history.

(56) References Cited

U.S. PATENT DOCUMENTS

| 5,334,303 A | 8/1994 | Muramatsu et al. |
| 5,460,710 A * | 10/1995 | Williams et al. .............. 205/780 |
| 2006/0094992 A1* | 5/2006 | Imboden et al. ................ 601/70 |

FOREIGN PATENT DOCUMENTS

| DE | 4040293 A1 | 6/1992 |
| EP | 0504730 A2 | 9/1992 |
| GB | 2297172 A | 7/1996 |
| JP | 56117161 A | 9/1981 |
| JP | 60015551 A | 1/1985 |
| JP | 01232248 A | 9/1989 |
| SU | 463636 A1 | 3/1975 |
| WO | 92/21961 A1 | 12/1992 |
| WO | 95/04271 A | 2/1995 |

OTHER PUBLICATIONS

Wang et al. Anal. Chem. 1995, 67, 1481-1485.*
Wang et al. Analytica Chimica Acta 310 (1995) 223-231.*
Teiji Kakizaki and Kiyoshi Hasebe: "Potentiometric stripping determination of heavy metals using a graphite-reinforcement carbon vibrating electrode", Fresenius' Journal of Analytical Chemistry, vol. 360, No. 2, Jan. 31, 1998, pp. 175-178, XP002447230, p. 175, col. 2—p. 176, col. 1; figure 1.

(Continued)

*Primary Examiner* — Jeffrey T Barton
*Assistant Examiner* — Steven Rosenwald

(57) ABSTRACT

The present invention relates to an electrochemical cell comprising a vibratile electrode (eg a vibratile microelectrode).

13 Claims, 4 Drawing Sheets

OTHER PUBLICATIONS

Shiela Schuette and Richard McCreery: "Efficient hydrodynamic modulation voltammetry with a microcylinder electrode", Analytical Chemistry, vol. 58, No. 8, Jul. 31, 1986, pp. 1778-1782, XP002447231 p. 1779, col. 2.

Figure 1:
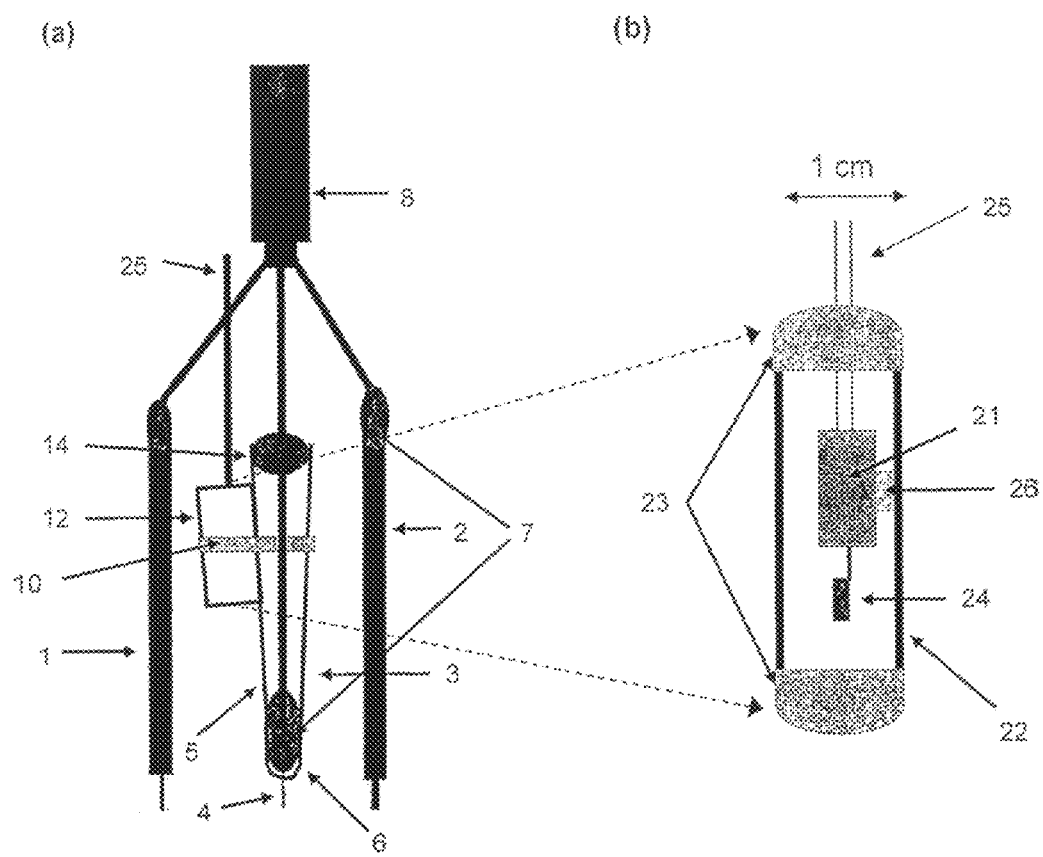

Kenneth Pratt and Dennis Johnson: "Vibrating wire electrodes—I literature review, design and evaluation" Electrochimica Acta, vol. 27, No. 8, Aug. 31, 1982, pp. 1013-1021, XP002447232, p. 1015, col. 2—p. 1018, col. 2; figure 1.

Joseph Wang, Eskil Sahlin and Jose Luis Lopez Paz: "Small-volume Elecrochemical Detection of Trace Nucleic Acids Using a Vibrating Electrode System",Electroanalysis 1999, 11, No. 5 pp. 380-383.

S. Bohm, H.N. McMurray, S. M. Powell, D.A. Worsley: "Photoelectrochemical Investigation of Corrosion Using Scanning Electrochemical Techniques", Electrochimica Acta 45 (2000) pp. 2165-2174.

* cited by examiner

ELECTROCHEMICAL CELL

CROSS-REFERENCE TO RELATED APPLICATIONS

This application is a 371 U.S. National Stage of International Application No. PCT/GB2007/001704, filed May 9, 2007 and published in English as WO 2007/135363 A1 on Nov. 29, 2007. This application claims priority to British Patent Application No. GB0609926.1, filed May 19, 2006. The disclosures of the above applications are expressly incorporated herein by reference.

The present invention relates to an electrochemical cell comprising a vibratile electrode (eg a vibratile microelectrode).

Natural water may have a very high ionic concentration (eg seawater) or low ionic concentration (freshwater) with variable levels of organic matter (eg 1-10 $mgL^{-1}$) and an extremely low concentration of some metals (typically $10^{-12}$ to $10^{-8}$ M). Metals at low concentrations such as iron and zinc are known micronutrients and play a key role in oceanic biogeochemical cycles whereas mercury, lead, cadmium, arsenic and copper are toxic.

Electrochemistry is one of the most sensitive and cost efficient ways to carry out trace metal (TM) analysis. The high sensitivity of commonly used electrodes for TM analysis is generally dependent on stirring the solution inside the electrochemical cell. This restricts analysis to the laboratory. The most common types of stirring are: a simple mechanically driven stirring bar in the solution containing the electrode or a rotating disc electrodes (RDE) either as a plain metal such as Au or Ag or with a film coating like Hg or Bi. With stirring, the electrodes will be able to detect TM with typical preconcentration times for one sample of 2 to 10 minutes. Without stirring, preconcentration times can be 15 minutes or more even with the most sensitive probes available for in-situ analysis.

The effect of stirring is a well documented phenomenon which enhances the rate determining step of the mass transfer of ions through a diffusion-controlled layer. The thicker the diffusion layer the slower the ions migrate to the electrode surface. For mechanical stirring, the thickness of the diffusion layer is typically 5 to 40 µm. Without stirring, the diffusion layer is an order of magnitude thicker. Other non-mechanical techniques which enhance mass transfer include exciting the water around the electrode either by using ultrasound (similar to an ultrasonic bath), microwaves or a heated wire electrode. With the possible exception of the heated wire, the use of these electrodes is restricted to the laboratory and in situ measurements are not feasible.

Vibrating electrodes have been exploited only in certain small volume, laboratory electrochemical procedures. For example, Wang et al (Electroanalysis, 1999, 11, 5) disclose small volume detection of nucleic acids using a carbon paste working electrode of 2.5 mm diameter packed in a Teflon sleeve. The sleeve is brought into transient contact with a vibrating mixer. Kakizaki et al (Fresenius J Anal Chem (1998), 360:175-178) disclose a potentiometric method for analysing heavy metals using a graphite-reinforced carbon electrode of diameter 0.5 mm which is vibrated by a piezoelectric bimorph oscillator. Bohm et al (Electrochimica Acta 45, 2000, 2165-2174) disclose a scanning vibrational electrode technique for photoelectrochemical investigation. Non-submersible electrodes fixed to vibrating equipment are disclosed in SU-A-463636, JP-A-01232248, JP-A-56117161, JP-A-60015551, GB-A-2297172 and WO-A-92/21961.

It is conventional wisdom that the excellent mass transport properties exhibited by microelectrodes renders redundant the need for electrolyte agitation. However this is not true for stripping techniques which require a deposition step. The present invention is based on the recognition that a vibratile microelectrode may be exploited to permit an electrochemical cell to analyse an electrolyte indigenously with much improved sensitivity.

Thus viewed from a first aspect the present invention provides an electrochemical cell for detecting the presence or amount of or changes in the amount of a metal species in an electrolyte comprising:

a working electrode adapted to be operationally submersible in the electrolyte, wherein the working electrode includes a vibratile electrode; and a reference electrode.

The electrochemical cell (or probe) of the invention may be advantageously used in the field to analyse environmental samples (eg freshwater samples such as river water or water in a distribution network or salt water samples such as sea water). The electrochemical cell of the invention permits low power, high resolution analysis of trace metals in situ enabling sensitive metal ion analysis underwater without long deposition times and without the need for bulky expensive equipment. Experiments indicate that the sensitivity of the working electrode is greater than can be achieved using ion selective electrodes, a rotating disk electrode or by stirring the electrolyte.

The metal species in the electrolyte may be a trace metal species. Typically the metal species is ionic.

The working electrode may be adapted to be operationally submersible to a depth of 1 cm or more, preferably 1 m or more, particularly preferably 10 m or more, more preferably 25 m or more, most preferably 40 m or more. The working electrode may be adapted to be operationally submersible in an electrolyte at a pressure of 4 Bar or more.

In a preferred embodiment, the electrochemical cell is monolithic. Particularly preferably the working electrode and reference electrode are partly embedded in a self-supporting insulating material, wherein the vibratile electrode is at least partially exposed from the insulating material to contact the electrolyte. The reference electrode may be at least partially exposed from the insulating material. The vibratile electrode may be exposed by a length of 2 mm or less. The monolithic electrochemical cell may be substantially waterproof. The insulating material may be epoxy.

In a preferred embodiment, the electrochemical cell further comprises: a counter electrode. The counter electrode may be vibratile. The counter electrode is typically an inert material (eg graphite or a metal such as platinum). The counter electrode may be in the form of a wire or coil. The counter electrode may be adapted to be operationally remote from the electrolyte. The counter electrode may be adapted to be operationally submersible in the electrolyte. The counter electrode may be embedded in a self-supporting insulating material (eg epoxy). The counter electrode may be at least partially exposed (eg by about 10 mm) from the insulating material.

The electrochemical cell may further comprise: a galvanostat adapted to apply a current to the working electrode.

In a preferred embodiment, the electrochemical cell comprises a potentiostat adapted to apply a potential to the working electrode. The potential may be constant, variable, stepped, pulsed or swept. The potentiostat may be adapted to measure current (eg current between the working electrode and counter electrode).

The electrochemical cell may be adapted to perform voltammetry (eg cyclic voltammetry, linear sweep or anodic stripping voltammetry), chronoamperometry, chronocoulometry or chronopotentiometry.

The electrochemical cell of the invention may be suitable for detecting the presence or amount of or changes in the amount of one or more of copper, mercury, arsenic, iron, lead, iodide, sulphide, cadmium or zinc species (eg ions) in the electrolyte.

The electrode may be microplanar. Preferably the electrode is a microwire electrode.

The electrode is typically composed of an inert material such as an inert metal (eg gold, silver or platinum) or mercury, amalgam or silver alloy. The electrode may be coated.

Preferably the vibratile electrode is a vibratile microelectrode. The dimension (eg diameter) of the microelectrode is typically 3 mm or less, preferably less than $10^{-5}$ m, particularly preferably less than 100 µm (eg about 25 µm).

In a preferred embodiment, the working electrode comprises:

a vibratory device in non-transient contact (eg direct or indirect contact) with the electrode. Preferably in this embodiment the working electrode is unitary and the vibratory device and electrode are supported or are self-supporting. For example, the vibratory device and electrode may be supported in non-transient contact by insulating material (eg epoxy). The non-transient contact may be permanent.

The working electrode may further comprise an open-ended elongate housing such as an elongate tube. The elongate housing may be waterproof. The electrode may be mounted (eg substantially coaxially mounted) in the elongate housing to project beyond a first open end. The first open end may be for example heat sealed. A second open end (opposite to the first open end) may be sealed. For example, the second open end may be fitted with a plug (eg an epoxy plug). The elongate housing may be tapered (eg convergent to the first open end).

The elongate housing may be polymeric (eg be composed of polyethylene). The vibratory device may be fixed securely to the elongate housing (eg by chemical or mechanical fixing means). The vibratory device may be fixed securely to the elongate housing by a fastener such as a tie.

The vibratory device may be an electrical or piezoelectrical vibratory device. The vibratory device may further comprise an enclosure (eg a tube). The enclosure is typically waterproof. For example, the enclosure may be composed of polyethylene. The enclosure may have a first open end opposite to a second open end. The first open end and second open end may be sealed. The first open end and second open end may be taped, coated or plugged (eg with epoxy) typically to allow any electrical connections to project beyond the enclosure.

In a preferred embodiment, the vibratory device is motor-driven. For example, a motor (eg a low voltage motor) may be confined in the enclosure. The motor is preferably driveable in the range 2 to 4 volts. The motor may be secured to an interior wall of the enclosure (eg by a mount such as an insulating mount for example an epoxy mount). The vibratory device may comprise an offset weight driven rotationally by a motor.

The vibratile electrode may be oscillatory or precessional. The motion of the vibrations may be random. The vibrations may have a frequency in excess of 100 Hz. Where the vibratory device is motor driven, the rotational frequency of the motor may be in the range 5000 to 15000 rpm.

The reference electrode may be vibratile. The reference electrode may be a calomel electrode, a silver/silver chloride electrode or platinum. The reference electrode may be adapted to be operationally submersible in the electrolyte. The reference electrode may be in the form of a wire.

The electrolyte is a conductive medium which may be selected from the group consisting of an aqueous solution (eg an aqueous solution of a base, acid or salt), an organic solvent and molten salt.

The working, reference and counter electrode may be electrically connected to a potentiostat or galvanostat by a metallic resin (eg a silver-loaded epoxy resin).

In a preferred embodiment of the invention, the electrochemical cell is monolithic and the working electrode, reference electrode and counter electrode are partly embedded in a self-supporting insulating material, wherein the vibratile electrode, reference electrode and counter electrode are at least partially exposed from the insulating material to contact the electrolyte.

Viewed from a further aspect the present invention provides the use of an electrochemical cell as hereinbefore defined for detecting the presence or amount of or changes in the amount of a metal species (eg trace metal species) in an electrolyte.

In a preferred embodiment of this aspect of the invention, the use for detecting the presence or amount of or changes in the amount of a metal species (eg trace metal species) in an electrolyte is by voltammetry (eg cyclic voltammetry, linear sweep or anodic stripping voltammetry), polarography (eg normal-pulse or differential-pulse polarography), chronoamperometry, chronocoulometry or chronopotentionmetry. Particularly preferred is anodic stripping voltammetry.

In a preferred embodiment of this aspect of the invention, the electrolyte is indigenous. The electrolyte is preferably seawater, freshwater, ocean water or domestic supply water (eg drinking water).

Viewed from a yet further aspect the present invention provides a working electrode as hereinbefore defined.

Figure 2:
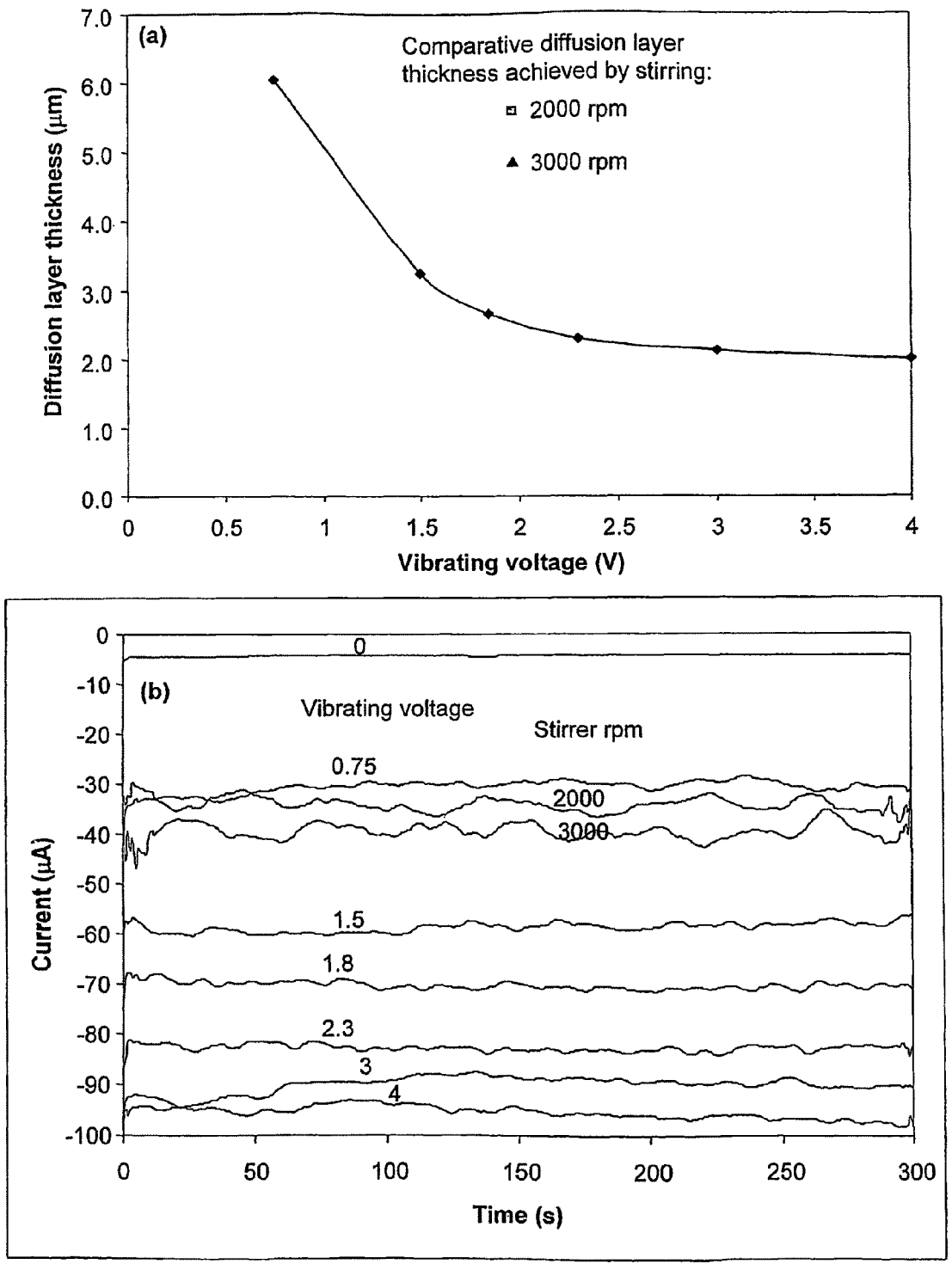
Figure 3:
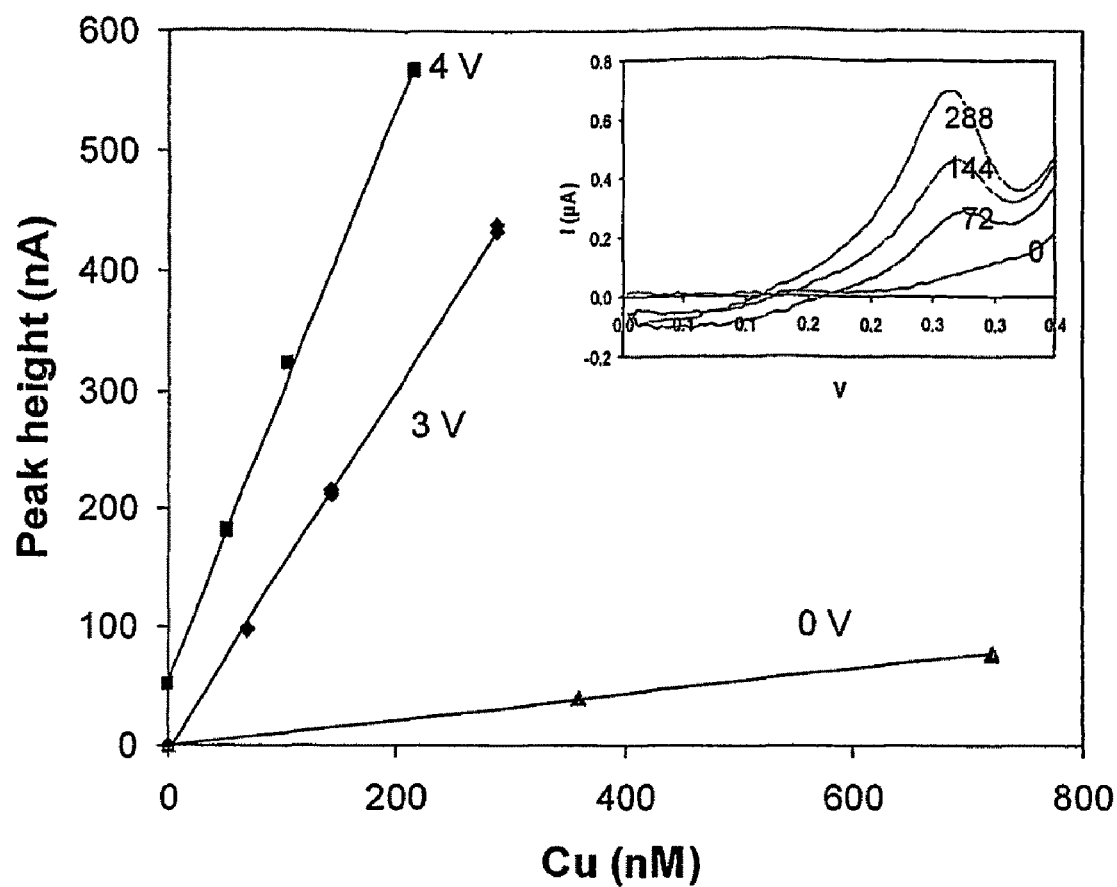
Figure 4:
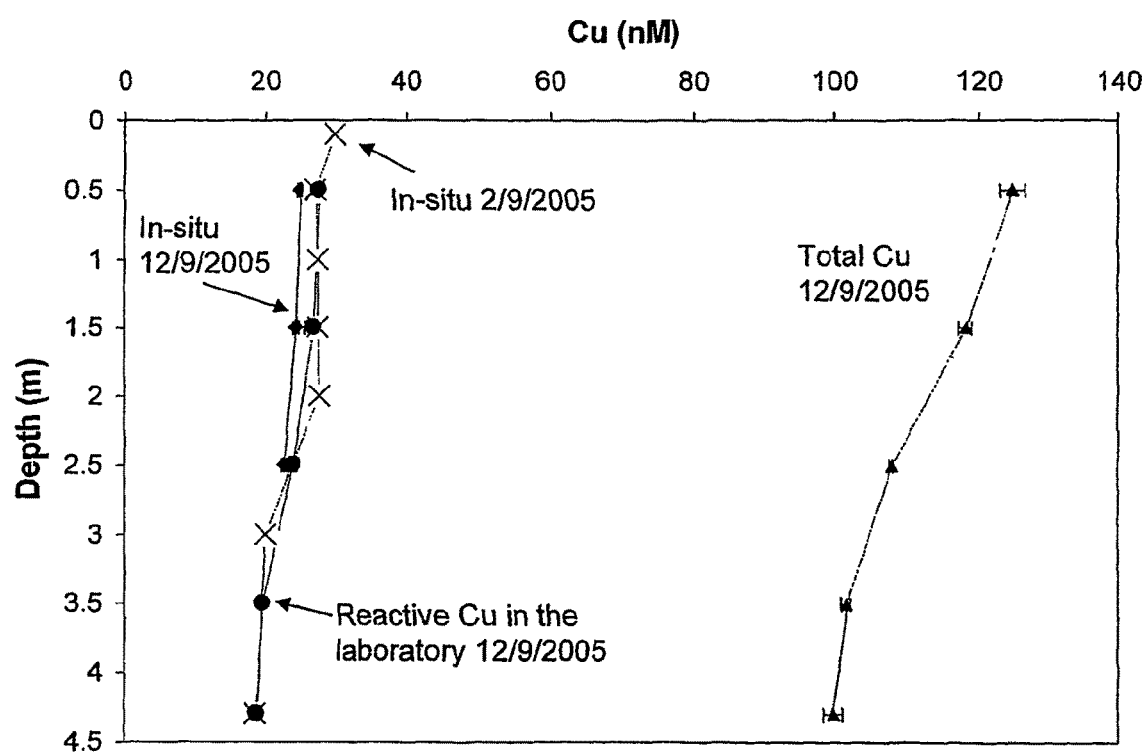

The invention will now be described in a non-limitative sense with reference to the accompanying Figures in which:

FIG. 1a: Schematic illustration of an embodiment of the electrochemical cell of the invention;

FIG. 1b: Isolated schematic illustration of the vibrator of the embodiment of FIG. 1a;

FIG. 2a: Graph showing the thickness of the diffusion layer as a function of vibrating potential;

FIG. 2b: Chronoamperometric curves obtained at different vibrating voltages;

FIG. 3 Graph showing calibration plots of copper with (3V, 4V) or without (zero) vibration of the electrode; and FIG. 4: Graph showing the results of two measurements of copper as a function of depth.

EXAMPLES

Experimental

Reagents

Metal stock solutions of copper ($Cu^{2+}$) and mercury ($Hg^{2+}$) were prepared by appropriate dilution of AAS metal standards (Fluka) using water from a Milli-Q system (Millipore) and acidified with additions of 20 µl of redistilled HCl to 20 ml. Preliminary experiments were carried out using sea water from the Atlantic (salinity 35, 0.1 µm filtered) which had been stored in a 50 L container in the laboratory or water from the Venice Lagoon (salinity 28, 0.2 µm filtered). Experiments at pH 2.5 were buffered using additions of 40% HCl (redistilled). To measure the size of the electrode diffusion layer, an aqueous solution was prepared from salts containing 10 mM $K_3Fe(CN)_6$ (BDH) and 0.5 M KCl (BDH).

Instrumentation

A Palmsens potentiostat (The Netherlands www.palmsens.com) with multi-mode and pA detection coupled to a laptop was used for all measurements and run on battery power (dry, 10 Ah, 6 V). Comparative measurements were carried out using a Metrohm VA 663 stand with the stirrer set between 2000-3000 rpm. The running of repetitive scans with blank subtraction was carried out with a modified version of the commercially available Ivium Palmsens PC.

With reference to the schematic illustration in FIG. 1a, an electrochemical cell (probe) comprises:
- a 500 µm diameter 99.99% platinum wire counter (counter) electrode 1 (Rasmussen AS, Norway)
- a reference electrode 2 which for the laboratory was a Ag/AgCl/Cl⁻ double junction (Metrohm) and for field work was an Ag wire 99.99% (Rasmussen AS, Norway) and
- a working electrode 3 comprising a gold microwire 4 of diameter 25 µm (Chempur).

For work in the laboratory, the electrodes 1, 2 and 3 were attached to a 1.5 m shielded conducting cable 8 (Farnell) using silver-loaded epoxy resin 7 (SL65, Rite Lok, UK). A 6 m cable 8 to the electrode was used in field work. The electrodes 1, and 2 were insulated from each other by individual coating with Araldite quick setting epoxy and electrode 3 by a casing and Araldite to leave exposed about 10 mm of the counter and working electrodes.

The working electrode 3 was constructed according to a method described in Billon et al, CMG 2004, Electroanalysis, 16(19):1583-15912. Briefly the method comprises melting a polyethylene pipette tip 5 in a tube furnace at 450° C. to seal the gold microwire 4 into the polyethylene pipette tip 5 projecting through a heat sealed end 6. About 2 cm of microwire 4 was normally used to ensure a working electrode 3 of about 0.3-5 mm length after trimming. The opposite end of the microwire 5 inside the polyethylene pipette tip 5 is connected (as described above) to the cable 8 which passes though an epoxy plug 14 to the potentiostat data cable 8. Fixed to the side of the working electrode 3 by a plastic tie 10 is a vibrator 12.

Vibrator Construction (FIG. 1b)

With reference to FIG. 1b, the vibrator 12 included a 3 V, 11500±2000 rpm motor 21 (JinLong Machinery) 1.6 cm in length and 0.5 cm in diameter. Vibrations are produced by spinning an off-set weight 24 on an axle. The speed (vibration intensity) can be changed using a variable resistor to adjust the drive voltage. The motor 21 was fitted to the inside of a polyethylene pipette tip 22 on an epoxy mount 26. The polyethylene pipette tip 22 was cut down to about 2 cm. The polyethylene pipette tip 22 was taped up on both ends with PVC tape 23 and covered with epoxy resin to leave protruding only the power supply wires 25. On setting, the vibrator 12 is waterproof.

Electrode Use

The working electrode was conditioned prior to measurements by cyclic voltammetry in 0.5 M $H_2SO_4$ using a 0.1 Vs⁻¹ scan rate with a step height of 5 mV, 15 cycles between 0 and 1.6V. All measurements were performed using subtractive anodic stripping voltammetry (SASV) in the square wave mode (SW) in which one scan is performed with deposition and one immediately afterwards with no deposition. The final scan is a resultant of subtracting the current values (y) of the scan with no deposition from the scan with deposition. The method used for calibration utilised preconcentration of the ion using underpotential deposition with deposition at −0.2 V for 1-5 min followed by 15 s at −0.8 V. The scan was performed after 4 s equilibration from 0 to 0.55 V using a frequency of 25 Hz, a step height of 4 mA and a pulse amplitude of 25 mV. An identical blank scan was performed immediately afterwards except there was conditioning for 20 s at 0.55 V and no deposition at −0.2 V. After completion of the blank scan, the cell was turned on at 0.55 V for cleaning of the electrode ready for the next measurement. All calibrations were carried out in UV digested seawater.

To measure the size of the diffusion layer, chronoamperometry was employed using a 10 mM $K_3Fe(CN)_6$/0.5 M KCl solution and the current was followed as a function of time for 5 minutes applying a potential of −0.3 V and sampling every 1 s. The experiment controlled automatically by the Palmsens software was carried out with and without vibrations. Employing steady state voltammetry and assuming a Nernst diffusion model, an estimate can be made of the diffusion layer thickness by using equation 1:

$$\delta = \frac{nFDAc_{bulk}}{I_{lim}} \quad (1)$$

where δ is the diffusion layer thickness (µm), $I_{lim}$ is the limiting current (A), n is the number of transferred electrons, F is the Faraday constant, D is the diffusion coefficient (cm²/s), A is the electrode area (mm²) and $C_{bulk}$ is the bulk concentration (moles/l).

Pressure Testing

The vibrator was housed in a hollow container so it was necessary to test how the probe would perform when exposed to increasing pressure in the water column. A 1 L wide mouthed polyethylene bottle (Nalgene) was used as the pressure container. Three holes were drilled in the lid to allow access for the gas tube and the electrode and vibrator wires. After pushing the cables through the top so the electrode would be inside the bottle, they were heavy sealed with a quick drying epoxy inside and outside the lid. The electrode and vibrator were then constructed on the end of the wires which will be inside the bottle. Teflon tape was used around the lid for an air tight seal. 500 ml of UV digested pH 2 seawater was added to the bottle. The bottle was sealed and the analysis was carried out at pressures from 1 atm (absolute) to 5 atm (equivalent to a depth of 40 m).

In-situ Analyses

The probe was tested from a pontoon in the Salthouse Dock of Liverpool Docks to a maximum depth of 4.5 m. Although historically very contaminated, the site is now cleaner, well oxygenated and has established benthic communities. The sensitivity of the probe for copper was calibrated in the laboratory before the measurements in bulk seawater. The calibration curves consisted of a blank with three additions of copper, each measured in triplicate. The sensitivity was re-calibrated after the in-situ measurements in water from the sample site to account for changes in the electrode response. Samples were taken at various depths at the same time as the main measurements and filtered in situ using a 0.2 µm cartridge filter (Sartorius, Sartoban 300). The samples were stored in the fridge and measured a day or so later.

Results and Discussion

After construction, the waterproofing on each vibrator was tested by submerging the unit in a large bucket filled with water to a depth of about 50 cm for 10 minutes while switched on. There was a visual check for signs of water ingress. By ensuring complete coverage of the housing and the power cable exit, all units were waterproof in these shallow depths. The motors used are very small and one 10 Ah, 6 V dry lead acid battery will power the potentsiostat and stirrer for 1-2 days depending on sampling frequency.

Estimation of the Diffusion Layer Thickness

By vibrating the working electrode, the diffusion layer thickness will decrease resulting in greater sensitivity. This works by increasing the mass transfer of analyte ions to the working electrode. Using a 2D-Nernst diffusion layer and Equation 1, the diffusion layer thickness was estimated from the pseudo steady-state current after 200 s electrolysis. FIG. 2a shows the diffusion layer thickness ($\delta$) as a function of vibration voltage. Points labelled 2000 and 3000 show the diffusion layer obtained using stirring of the solution at 2000 and 3000 rpm respectively. For non-vibrated electrodes (not shown), the diffusion layer thickness $\delta$=43±0.4 µm. At maximum drive (4V), $\delta$=2.0±0.2 µm (an increase by a factor of 22). This is a very small diffusion layer and is equivalent to that theoretically provided by a Rotating Disc Electrode (RDE) running at an unrealistic speed of 30000 rpm. For common analytical conditions, $\delta$ referred to above is smaller than a previously reported value ($\delta$=4.5 µm) attained for a RDE set at 9000 rpm (Bonfil et al, Analytica Chimica Acta, 387:85-95).

FIG. 2a shows there is little difference in $\delta$ when working within the manufacturers recommended voltages of 2V (2.7 µm) and 4V (2.0 µm). On this basis, 3V was chosen for further experiments. Choosing a drive potential between 2 and 3V will lower the power consumption and should not significantly effect the sensitivity.

FIG. 2b shows the actual scans achieved by the various vibration intensities. The scans are noisy but this is because the electrode is moving. This experiment was run over 300 s and any decrease in performance of the stirrer would have shown as a decreasing $I_{lim}$. It can be seen that all lines are straight for the duration of the experiment and the experiments were run consecutively with a one minute interval giving a total run time of 1800 s (30 minutes). Thus it is clear that even after 1800 s of almost continual use there is no drop in performance of the vibrator.

The Effect of Vibration on Sensitivity

It has been shown that the vibrator will greatly increase the steady state current and decrease the diffusion layer thickness of the electrode. This should translate to greater sensitivity of the electrode to the analyte (in this case copper). FIG. 3 shows standard additions of copper to pH 2.5 UV digested seawater and the inset is the subtracted scans from the calibration. Conditions are: UV digested seawater with 0.01 M HCL, conditioning at 0.55V for 20 s, deposition at −0.2 V for 45 followed by 15 s at −0.8 V, 4 s equilibration and scan from 0 to 0.55 V using a frequency of 25 Hz, step height of 4 mA and a pulse amplitude of 25 mV. The blank scan was the same except conditioning for 20 s at 0.55 V and no deposition at −0.2 V. The standard deviation of repetitive copper determinations (n=5) was within ±5% and linear regression of the calibrations gave $r^2$ values of 0.999 or better. The gradient of the calibration slope (sensitivity) for different stirring potentials is shown in Table 1.

TABLE 1

A comparison of different vibration intensities (volts) and their effect on the copper sensitivity of the probe

|  | No Vibration | Stirred Solution | 3 V Vibration | 4 V Vibration |
| --- | --- | --- | --- | --- |
| Sensitivity (nA/nM) | 0.11 | 0.45 | 1.5 | 2.4 |
| Factor Increase | — | 4 | 14 | 22 |

Table 1 highlights the effectiveness of vibrating the electrode. The sensitivity increased by a factor of 22 by vibration at 4V compared with a factor of 4 by stirring the solution using a rotor at 3000 rpm. At 3V vibrations, the electrode is three times more sensitive than by solution stirring and at 4V this increases to a factor of four. The extra sensitivity of the electrode is a result of the high frequency vibrations ($\approx$11000 rpm) significantly enhancing the hydrodynamic conditions around the electrode and mass transport to it. The vibrations are so fast that when visually inspecting the electrode during use, it is difficult to see the tip moving.

It is noteworthy that the sensitivity varies between vibrating probes and the key factors appear to be the probe weight and stiffness. These two are related because when preparing probes for in situ work as described above, extra epoxy was applied to the probe as a waterproofing precaution. This adds to the probe weight and because it is constructed of three wires extending from their outer core, the extra epoxy stiffens the wires dampening the vibrations. The effect of this is to reduce the increase in sensitivity factor from 14 for a very flexible probe (Table 1) to about 8 for a stiffened submersible probe. Optimisation of the probe construction for in situ analysis should enable sensitivities close to those achieved in the laboratory.

Determination of Electrochemically Labile Copper in Seawater

The probe was tested in conditions found in common aquatic environments. This was a brief test using seawater at natural pH from the Venice Lagoon (salinity=29). Small additions of metal (0.1 to 1 nM) to the sample for calibrations will be quickly complexed to organic matter so the probe was externally calibrated in a separate solution of UV digested seawater. The sensitivity of the electrode was 8.25 nA/nM for 5 min deposition giving an approximate limit of detection (LOD) of 15 µM (estimated using the noise and the variability of the copper peak). This LOD is similar to that of a 5 µm diameter Au-wire after 10 minutes deposition from stirred solution (10 µM) and better than an Ir-microarray (0.18 nA/nM) after 15 min deposition. The concentration of electrochemically labile copper in Venice Lagoon water was 1.8 nM which is comparable to other in situ studies of copper in the lagoon. 1.8 nM is equivalent to about 10% of the total copper of this sample measured by traditional electrochemical techniques after UV digestion of the sample.

In an attempt to increase the sensitivity of the electrode, the deposition potential was set at −0.8 V for the duration of the preconcentration stage. At more negative potentials than −0.2 V organically bound copper becomes increasingly released and available for detection. The effect was a doubling of the peak height in the seawater at natural pH. This can be attributed to the breaking of copper-organic complexes because in UV digested seawater, the deposition potential has no significant effect on the peak height for copper.

Pressure Testing

The probe was placed inside a water-filled container which could be pressurised internally to evaluate whether underwater measurements could be performed. The probe performed consistently throughout the experiment up to the maximum achievable pressure equivalent to a depth of 40 m (4 Bar above ambient pressure).

Field Testing

The field test sample site was a pontoon at Salthouse Dock which is part of the Albert Docks, Liverpool. Samples were taken at various depths to a maximum of 4.5 m and in situ measurements were made at the same depths using the vibratile electrode. Shown in FIG. 4 are the results of a first trip (squares) starting at 14.30 and a second trip (diamonds) starting at 14.30 ten days later. Circles denote samples run in the laboratory from the first trip and triangles denote the total dissolved topper (UV digested) concentration of the first trip. Conditions were: 30 s conditioning at 0.55, deposition at −0.8 V for 120 s, 4 s equilibration and scan from 0 to 0.55 V at a square-wave frequency of 25 Hz, step height of 4 mV and a pulse amplitude of 25 mV. The blank scan was the same except for conditioning for 5 s at 0.55 V and deposition at −0.8 V for 15 s. Error bars are the SD of 3 replicates.

The profile for the first trip shows a copper maximum at the surface of 30 nM dropping to 19 nM for the bottom water. The profile for the second trip stops at 3 m because at 4 m depth the probe picked up a sticky organic substance on the Au wire. This prevented reliable measurements but samples taken at the same time and run back in the laboratory (circle) show a trend of decreasing copper with depth similar to the trend with the first trip.

Agreement between field and laboratory measurements was good (within 10%). However there was a large difference between the measurements in untreated and UV-digested water. UV digestion caused the detected copper to increase from 26 to 100-120 nM. The total dissolved copper shows a trend of decreasing copper concentration with increasing depth. The field work was undertaken using a deposition potential of −0.8 V and the percentage of labile to total copper was 21±2%. The in situ measurements produced different peak potentials than after UV digestion in the laboratory. For the top 2.5 m, there is a 30 mV positive shift from UV digested, natural pH water. The probe showed a further 60 mV positive shift at depths of 3 and 4 m which upon return to the surface, reverted to the original peak height and position. A positive peak potential shift could indicate problems with the reference electrode or a lower concentration of complexing ligands. The probe uses a pseudo reference electrode which is sensitive to salinity changes. If the potential shift was due to changes in salinity, the Nernst equation predicts that this would require a salinity change from 35 to 17. This large salinity change has not been recorded for Salthouse dock with the largest recorded range being 25.3 to 28.7. During the summer, the water is topped up daily and there has been no previous evidence for stratification or anoxia within the docks so it is unlikely salinity/stratification is responsible for the shift.

SUMMARY

A microwire electrode was made to vibrate by fixing to an asymmetric rotor spinning at about 100 Hz. The motor was waterproofed by encasing and coating with epoxy. Preliminary experiments showed that the vibrating working electrode can be used to a water pressure of 4 Bar (equivalent to a depth of 4 m). Comparative measurements showed that the vibrating electrode is 3 to 4 times more efficient than stirring using a rotor at 3000 rpm and has a thinner diffusion layer (2 μm) than a rotating disk electrode. The vibratile working electrode enhances the sensitivity of an unstirred electrode by a factor of 22 with a SD of <5% for repeated calibrations (n=5). The sensitivity for copper was 2 nA/nM for two minutes deposition giving a limit of detection of ~30 μM Cu.

The invention claimed is:

1. An electrochemical cell for detecting the presence or amount of or changes in the amount of a metal species in an electrolyte comprising:
   a working electrode adapted to be operationally submersible in the electrolyte, wherein the working electrode comprises: a vibratile electrode and a vibratory device in non-transient contact with the vibratile electrode, wherein the working electrode is unitary and the vibratory device and vibratile electrode are supported by insulating material, wherein the vibratory device comprises an enclosure and a motor secured to an interior wall of the enclosure to generate vibrations and an offset weight driven rotationally by the motor; and
   a reference electrode.

2. The electrochemical cell as claimed in claim 1, wherein the working electrode is adapted to be operationally submersible to a depth of 40 m or more.

3. The electrochemical cell as claimed in claim 1, wherein the working electrode and reference electrode are partly embedded in a self-supporting insulating material, wherein the vibratile electrode is at least partially exposed from the insulating material to contact the electrolyte.

4. The electrochemical cell as claimed in claim 3, wherein the reference electrode is at least partially exposed from the insulating material.

5. The electrochemical cell as claimed in claim 1, further comprising: a potentiostat adapted to apply a potential to the working electrode.

6. The electrochemical cell as claimed in claim 1, wherein the metal is selected from the group consisting of copper, mercury, arsenic, iron lead, cadmium and zinc.

7. The electrochemical cell as claimed in claim 1, wherein the vibratile electrode is a microwire electrode.

8. The electrochemical cell as claimed in claim 1, wherein a dimension of the vibratile electrode is less than 100 μm.

9. The electrochemical cell as claimed in claim 1, wherein the working electrode further comprises; an open-ended elongate housing in which the vibratile electrode is mounted to project beyond a first open end and to an exterior of which the vibratory device is fixed securely.

10. The electrochemical cell as claimed in claim 1, wherein the reference electrode is adapted to be operationally submersible in the electrolyte.

11. The electrochemical cell as claimed in claim 1, further comprising: a counter electrode.

12. The electrochemical cell as claimed in claim 11 being monolithic, wherein the working electrode, reference electrode and counter electrode are partly embedded in a self-supporting insulating material and the vibratile electrode, reference electrode and counter electrode are at least partially exposed from the insulating material to contact the electrolyte.

13. The electrochemical cell as claimed in claim 1, wherein the insulating material is a self-supporting insulating material and the working electrode and reference electrode are partly embedded in the self-supporting insulating material, wherein the vibratile electrode is at least partially exposed from the self-supporting insulating material to contact the electrolyte.

* * * * *